(12) United States Patent
Igari et al.

(10) Patent No.: US 6,486,099 B2
(45) Date of Patent: Nov. 26, 2002

(54) MICROCAPSULE AND PROCESS FOR PRODUCTION THEREOF

(75) Inventors: Yutaka Igari, Fukushima-ken (JP); Yuzi Hori, Fukushima-ken (JP); Tsuneo Okamoto, Fukushima-ken (JP)

(73) Assignee: Kureha Kagaku Kogyo Kabushiki Kaisha, Tokyo (JP)

( * ) Notice: Subject to any disclaimer, the term of this patent is extended or adjusted under 35 U.S.C. 154(b) by 4 days.

(21) Appl. No.: 09/758,167

(22) Filed: Jan. 12, 2001

(65) Prior Publication Data
US 2001/0008874 A1 Jul. 19, 2001

(30) Foreign Application Priority Data
Jan. 13, 2000 (JP) ......................................... 2000-004370

(51) Int. Cl.$^7$ ............................. A01N 25/28; B01J 13/08
(52) U.S. Cl. ........................... 504/359; 514/963; 264/4; 427/213.31; 427/213.34; 427/214
(58) Field of Search .................. 504/359; 514/963; 264/4; 427/213.31, 213.34, 214

(56) References Cited

U.S. PATENT DOCUMENTS

| | | | |
|---|---|---|---|
| 4,557,755 A | 12/1985 | Takahashi et al. | ............. 71/100 |
| 5,180,637 A | 1/1993 | Sumii | ................... 428/402.21 |

FOREIGN PATENT DOCUMENTS

| | | |
|---|---|---|
| CA | 2131548 | 9/1993 |
| GB | 1 502 440 | 3/1978 |
| GB | 2 073 697 | 10/1981 |
| GB | 2 107 480 | 4/1983 |

Primary Examiner—S. Mark Clardy
(74) Attorney, Agent, or Firm—Wenderoth, Lind & Ponack, L.L.P.

(57) ABSTRACT

A microcapsule (or microencapsulated product) having a uniform and smooth coating film and also an excellent performance of gradually liberating the content material is produced at a good particle size distribution while suppressing the occurrence of isolated or aggregated film material, aggregated microcapsules and isolated core material. The production process includes: a first coating step of mixing a water-soluble cationic amino resin and an anionic surfactant in the presence of a hydrophobic core material dispersed in an aqueous medium to coat the dispersed core material with a coacervate of the cationic amino resin and the anionic surfactant; and a second coating step of adding an amino resin prepolymer into an aqueous dispersion liquid containing the coated dispersed core material and polycondensating the amino resin prepolymer to further coat the coated dispersed core material with a polycondensate of the amino resin prepolymer.

18 Claims, 5 Drawing Sheets

MICROCAPSULE AND PROCESS FOR PRODUCTION THEREOF

FIELD OF THE INVENTION AND RELATED ART

The present invention relates to a microcapsule (or microencapsulated) product enclosing a core material of a hydrophobic material which is solid or liquid at room temperature, and a (continuous) process for microencapsulation for production thereof. More specifically, the present invention relates to a microcapsule of a hydrophobic material having a stable (laminar) coating structure, and a (continuous) process for production thereof.

Microencapsulation technique is widely adopted for the purpose of, e.g., protection of or controlling the rate of liberation to outside of a comminuted core material or content.

For example, as microencapsulation processes for agricultural chemicals, there have been proposed processes using, e.g., gelatin which is a water-soluble polymer (e.g., Japanese Laid-Open Patent Application (JP-A) 50-99969), polyamide, polyurethane or polyester (JP-A 54-135671), polyvinyl acetate or polyvinyl ether (JP-A 55-92136), polyurethane-polyurea (JP-A 54-91591), and polyamide-polyurea (JP-A 48-4643), respectively, as coating film materials. However, a microcapsule using gelatin as the film material is poor in controllability of persistent chemical effect due to the fact that the film in a dry state becomes too tight to allow liberation of the content and the film in a wet state is swollen to liberate most of the content in a short time. Further, a microcapsule obtained by once-forming a film of a water-soluble polymer such as gelatin and making the film tighter by reacting the film with, e.g., an aminoplast resin prepolymer (JP-A 52-38097) cannot be free from the drawback of liberating the content in a short time in a wet state. Microcapsules comprising film materials of polyurea, polyamide, polyurethane, etc., are produced by interfacial polymerization, for which one of the monomers for constituting the film polymer has to be soluble in the core material and which is therefore not applicable to a core material not having an ability of dissolving the monomer. Further, the interfacial polymerization has drawbacks that some portion of the monomer can remain unreacted to adversely affect the core material capable of dissolving the monomer and the effect of the core material is reduced when the core material is reactive with the monomer.

Other microencapsulation processes include a process of using urea-formamide polycondensate alone (Japanese Patent Publication (JP-B) 46-30282); and a process of dispersing a material to be encapsulated in a dispersion medium in the presence of a reactive tenside, then irreversibly converting the tenside into an insoluble state to form a primary capsule suspension liquid, mixing an aminoplast precondensate solution into the primary suspension liquid and converting the aminoplast precondensate into an insoluble state to form a secondary capsule suspension liquid containing microcapsules provided with a reinforced coating film wall (JP-A 46-7313). However, the latter process using an aminoplast precondensate for forming a film wall is inevitably accompanied with aggregation of the produced microcapsules to result in aggregated particles. As a result, it becomes very difficult to control the rate of liberation of the core material and to recover the microcapsules in an isolated powdery state.

As for a microcapsule comprising a core material uniformly coated with a film material of an amino resin, such as melamine resin, (thio)urea resin or benzoguanamine resin, the applicant company (Kureha Kagaku Kogyo K.K.) has already proposed a process for producing a microcapsule comprising a film material of an amino resin and a water-soluble cationic resin in the presence of an anionic surfactant (JP-B 2-29642, U.K. Laid-Open Patent Application (GB-A) 2113170). According to the process, polycondensation of an amino resin prepolymer is caused in the co-presence of minor amounts of a water-soluble cationic resin and an anionic surfactant which have mutually opposite polarities of charges, whereby it becomes possible to form a dispersion liquid which is much stabler than in the absence of the latter two materials, thus providing uniform microcapsules.

According to further study of the present inventors, however, the uniformity of the capsule coating layer obtained by the process of the above-mentioned GB-A 2113170 is not necessarily sufficient, and the occurrence of a substantial amount of isolated or aggregated particles of the film material alone not containing the core material can still be recognized together with the occurrence of aggregated microcapsules and uncoated particles of the core material. The isolated or aggregated particles of the film material alone and aggregated microcapsules can be separated from the product microcapsule, but this results in a lower yield of the product along with the presence of isolated core material, and the insufficient uniformity of the coating layer naturally results in a lowering in product performance.

SUMMARY OF THE INVENTION

A principal object of the present invention is to provide a microcapsule having a more uniform coating layer on a hydrophobic core material, and also a process for effectively producing such a uniform microcapsule with extreme suppression of the occurrence of isolated or aggregated film material alone, aggregated microcapsules and isolated core material.

According to our further study, for accomplishing the above object, it has been found very effective to use a water-soluble cationic amino resin and an anionic surfactant (used as agents for improving the affinity between an amino resin prepolymer and core material particles in the above-mentioned process of JP-B 2-29642) as agents for forming a coacervate film coating core material particles prior to addition of an amino resin prepolymer to coat the core material particles successively with a solidified layer of the coacervate and a polycondensate of the amino resin prepolymer.

Thus, according to a first aspect of the present invention, there is provided a microcapsule, comprising a particulate core material, and a laminar coating layer including (i) a solidified layer of coacervate of a water-soluble cationic amino resin and an anionic surfactant, and (ii) a layer of polycondensate of amino resin prepolymer, successively coating the particulate core material.

According to a second aspect of the present invention, there is provided a process for producing a microcapsule, comprising:
 a first coating step of mixing a water-soluble cationic amino resin and the anionic surfactant in the presence of a hydrophobic core material dispersed in an aqueous medium to coat the dispersed core material with a coacervate of the cationic amino resin and the anionic surfactant, and
 a second coating step of adding an amino resin prepolymer into an aqueous dispersion liquid containing the coated dispersed core material and polycondensating the amino resin prepolymer to further coat the coated dispersed core material with a polycondensate of the amino resin prepolymer.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1:
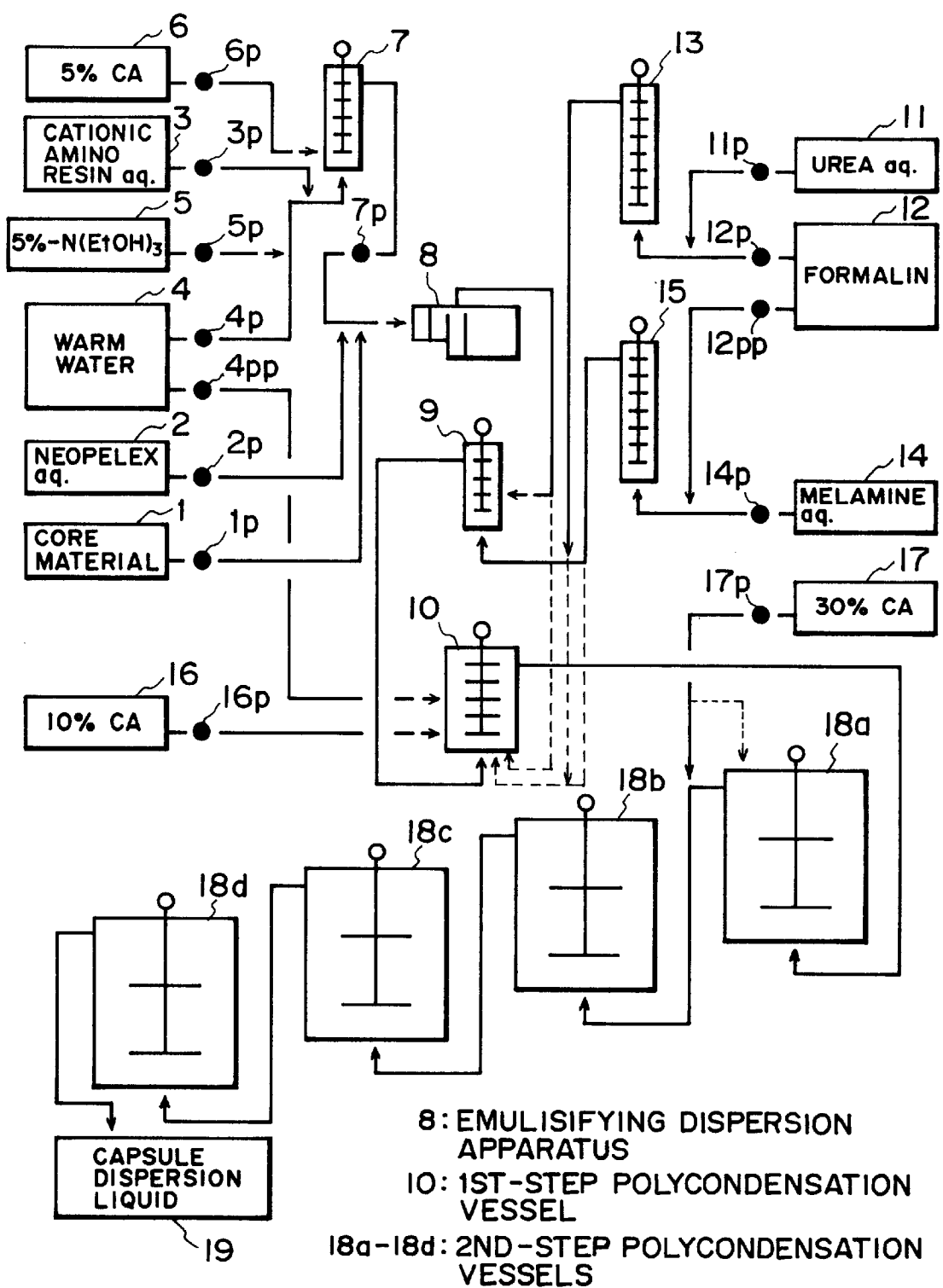
FIG. 1 is a schematic diagram for illustrating an apparatus system for practicing an embodiment of the process for producing a microcapsule according to the invention.

A preferred embodiment of the process for producing a microcapsule according to the present invention will now be described more specifically with reference, as occasion demands, to FIG. 1 which illustrates an apparatus system for practicing the embodiment.

<First Coating Step>

In a first coating step, a water-soluble cationic amino resin and an anionic surfactant are mixed with each other in the presence of a hydrophobic core material dispersed in an aqueous medium to coat the dispersed core material with a coacervate of the cationic amino resin and the anionic surfactant. In the apparatus of FIG. 1, this is effected by introducing the above-mentioned materials into a emulsifying dispersion apparatus (8) (a preferred example of which is a horizontal high-speed shearing-type stirrer ("TK Hi-line Mill" made by Tokushu Kika Kogyo K.K.)) for dispersion mixing of the materials.

More specifically, a core material (1) dispersed in a water-insoluble solvent, as desired, and an anionic surfactant aqueous solution (2) are supplied in a desired ratio to the emulsifying dispersion apparatus 8 through respective metering pumps (1p and 2p). On the other hand, a water-soluble cationic amino resin (3) as another component for forming the coacervate is supplied together with warm water (4) and a pH buffer agent aqueous solution (5) (e.g., 5%-aqueous solution of triethanolamine (N(EtOH)$_3$) continuously through respective metering pumps (3p, 4p and 5p) to an emulsion mother liquid mixing vessel (7), wherein they are uniformly mixed withe each other. Simultaneously therewith, an acid catalyst (6) (e.g., 5%-aqueous solution of citric acid (CA)) is supplied through a metering pump (6p) to the mixing vessel (7) for continuously adjusting the pH of the mixture liquid to form an emulsion mother liquid. The thus-formed emulsion mother liquid is introduced through a meterin pump (7p) together with the above-mentioned core material (1) and anionic surfactant aqueous solution (2) into the emulsifying dispersion apparatus (8), so that they are mixed with each other, preferably immediately before shearing and stirring teeth in the emulsifying dispersion apparatus (8). As a result, owing to high-speed dispersion stirring in the emulsifying dispersion apparatus (8), the particles of the hydrophobic core material are coated with a coacervate of the cationic amino resin and the anionic surfactant which has been solidified to some extent.

Next, some detailed features of the first coating step will be supplemented.

(Core Material)

As a preferred class of examples of hydrophobic material constituting the core material (1), agricultural chemicals including insecticides, fungicides, herbicides, virucides and attractants, are enumerated. Other examples of the hydrophobic material suitable for microencapsulation may include lubricants, inorganic materials, color formers, adhesives and perfume. These hydrophobic materials may be either solid or liquid. Specific examples of hydrophobic materials suitable for microencapsulation may include: as agricultural chemicals, insecticides, such as chlorpyrifos, ethoprophos, NAC (carbaryl), BPPS (propargite), MEP (fenitrothion), diazinon, DDVP (dichlorvos), chlorobenzilate, propaphos, disulfoton, CVP (chlorfenvinphos), CVMP (tetrachlorvinphos), CYAP (cyanophos), isoxathion, pyridaphenthion, chlorpyrifos-methyl, malathion, PAP (phenthoate), DMTP (methidathion), sulprofos, pyraclofos, DEP (trichlorfon), EPN, MIPC (isoprocarb), BPMC (fenobucarb), XMC, carbosulfan, benfuracarb, furathiocarb, fenpropathrin, fenvalerate, cycloprothrin, ethofenprox, silafluofen, bensultap, imidacloprid, acetamiprid, buprofezin, endosulfan, fipronil, chlorfenapyr, DCIP, fosthiazate, natural pyrethrins, and synthetic pyrthrins, such as allethrin and tralomethrin; fungicides, such as probenazole, isoprothiolane, IBP (iprobenfos), EDDP (edifenphos), iminoctadine albesilate, TPN (chlorothalonil), BCM (benzimidazole), dichlofluanid, TBZ (thiabendazole), oxine-copper, zineb, maneb, mancozeb, thiram, tolclofosmethyl, fthalide, pyroquilon, carpropamid, thiophanate-methyl, iprodione, benomyl, procymidone, mepronil, flutolanil, triflumizole, prochloraz, azoxystrobin, kresoxim-methyl, metominostrobin, dazomet, diclomezine, pencycuron, and dithianon; herbicides, such as, butachlor, oxadiazon, bentazone, DBN (dichlobenil), pyributicarb, ACN (quinoclamine), clomeprop, naproanilide, cyhalofop-butyl, quizalofop-ethyl, phenmedipham, thiobencarb, orbencarb, molinate, thenylchlor, bromobutide, mefenacet, cafenstrole, asulam, DCMU (diuron), linuron, daimuron, bensulfuron-methyl, pyrazosulfuron-ethyl, imazosulfuron, atrazine, ametryn, PAC (chloridazon), bentazone, pyrazolynate, pyrazoxyfen, benzofenap, trifluralin, benfluralin, pendimethalin, piperophos, butamifos, glyphosate-isopropylammonium, glufosinate-ammonium, DCBN (chlorthiamid), and sethoxydim; biotic agricultural chemicals, such as BT (bacillus thuringiensis berliner); attractants, such as codlelure surflure, smalure and phycilure; plant growth inhibitors, such as forchlorfenuron, uniconazole, and piperonyl butoxide; rodenticides, such as coumatetralyl and chlorophacinone; and repellents.

The above-mentioned names of effective components of agricultural chemicals are general names listed in "Agricultural Chemical (Nohyaku) Handbook 1998-edition" published from Nippon Shokubutsu Boeki Kyokai, Japan.

Examples of hydrophobic core materials other than agricultural chemicals may include: lubricants, such as gear oil, machine oil, silicone oil, wax and liquid paraffin; inorganic materials, such as titanium oxide, barium titanate, and toner (magnetic powder); fluorine-containing resins, such as PTFE (polytetrafluoroethylene); color formers, such as leuco dyes, dyes, pigments and printing inks; detector agents, such as paradium compounds (leaked hydrogen detector) and bromine compounds (ammonium detector);

and catalysts including vulcanization promoters, such as PX (zinc N-ethyl-N-phenyldithiocarbamate) added to rubber and anti-weathering agents, such as PA(1-(N-phenylamino)-napthalene) and AD (dialkyldiphenylamine) (added, e.g., to tires, particularly two-layered tires and shoe-sole rubber; additives (plasticizers) to plastics and rubbers, such as DEP (diethylphthalate), BPO (benzoyl peroxide), DBF (dibutyl fumarate), DBS (dibutyl sebacate), thiokol TP; blowing agents (volatile organic solvents), perfume, and medicines.

These hydrophobic materials may ordinarily be microencapsulated for respective species individually, but can be microencapsulated in two or more species together if they are chemically stable in the co-presence. Further, in the case where the hydrophobic core material is liquid, it can be dissolved in a water-insoluble solvent, such as xylene, toluene, kerosene or vegetable oil, for the purpose of alleviating the odor, toxity, volatility, etc. In the case where the hydrophobic core material is solid, the core material can be microencapsulated as it is, or after being melted by heating to a temperature above its melting point, or after being dissolved in a water-insoluble solvent, such as xylene, toluene or kerosene.

(Anionic Surfactant)

The anionic surfactant (2) is used to form a coacervate primarily coating the core material particles together with a water-soluble cationic amino resin described hereinafter. Examples thereof may include: aliphatic acid salts, higher alcohol sulfate ester salts, alkylbenzenesulfonic acid salts, naphthalenesulfonic acid-formalin condensates, and alkyl-naphthalenesulfonic acid salts, while sodium dodecylbenzenesulfonate (e.g., "NEOPELEX", made by Kao K.K., as an example of commercial product) is most preferred. The anionic surfactant may preferably be used in 0.05–0.8 wt. part, particularly 0.10–0.40 wt. part, per 100 wt. parts of the core material. (Water-soluble cationic amino resin)

The water-soluble cationic amino resin (3) is a water-soluble amino resin prepolymer obtained by converting an amino resin prepolymer (namely, a prepolymer of (thio)urea (-formaldehyde) resin, melamine(-formaldehyde) resin or benzoguanamin(formaldehyde) resin) as used in a second coating step described hereinafter by reaction with a cationic modifier agent. For example, urea-formaldehyde resin prepolymer may be subjected to polycondensation in a known manner together with a cationic modifier agent, such as diethylenetriamine, triethylenetetramine, tetraethylenepentamine, guanidine; dicyandiamide, guanylurea, dicyandiamide formate, dimethylaminoethanol, diethylaminoethanol, diethanolamine, oxazolidine, polyphenyl-biguanide or the like. A particularly preferred example thereof may be urea-formaldehyde resin prepolymer modified with diethylenetriamine, triethylenetetramine or tetraethylenepentamine (a representative commercially available product of which may be diethylenetriamine-modified product, available under a trade name of "U-RAMIN P-1500", from Mitsui Kagaku K.K.). The water-soluble cationic amino resin may preferably be used in 5–50 wt. parts, particularly 10–25 wt. parts, per 100 wt. parts of the core material.

(Acid Catalyst)

The acid catalyst (6) is added to adjust the pH of the dispersion liquid in the emulsifying dispersion apparatus (8) to a value of 3–9, preferably 3–7, more preferably 4–6, thereby forming a moderately solidified coacervate film on the core material particles. Examples thereof may include: organic acids, such as formic acid, acetic acid and citric acid; inorganic acids, such as hydrochlorin acid, sulfuric acid, nitric acid and phosphoric acid; and acidic or readily hdro-lyzable salts, such as aluminum sulfate, titanium oxychloride, magnesium chloride, ammonium chloride, ammonium nitrate, ammonium sulfate and ammonium acetate. These acid catalysts may be used singly or in mixture of two or more species. Among the above, acetic acid, hydrochloric acid, sulfuric acid and citric acid are preferred as the acid catalyst, and citric acid is particularly preferred in view of easiness of pH adjustment, and performances of suppressing the occurrence of isolated core material particles and aggregation of microcapsules. If the pH of the dispersion liquid in the first coating step is outside the above-mentioned ranges, the aggregation of the core material particles coated with the coacervate film is liable to occur.

(Order of Mixing)

In the apparatus system example shown in FIG. 1, for the mixing of the water-soluble cationic amino resin (3) and the anionic surfactant (2), the core material (1) is first mixed with an aqueous solution of the anionic surfactant (2). This mode is desirable for uniform coacervate coating of the core material particles, but it is also possible to first mix the core material (1) with an aqueous solution of the water-soluble cationic amino resin (3), and then mixing the resultant mixture liquid with an aqueous solution of the anionic surfactant (2). In the case where the cationic amino resin and the anionic surfactant having mutually different signs of charges are co-present, the coacervate formation is liable to be ununiform to result in formation of much aggregated particles, if the time of co-presence before the dispersion of these materials is prolonged. The mixing time, i.e., the time of co-presence, until the dispersion should be suppressed to at most 10 seconds, preferably at most several seconds, particularly preferably at most 1 second.

(Dispersion Conditions)

Preferred conditions for dispersion of the hydrophobic core material in the emulsifying dispersion apparatus (8) may include a temperature of 20–70° C., more preferably 30–50° C., and the stirring intensity in the case of a liquid core material may preferably be set to provide a coacervate-coated dispersion particle diameter (droplet diameter) of 1–100 $\mu$m, preferably 1–50 $\mu$m, more preferably 2–20 $\mu$m, particularly 2–10 $\mu$m in view of the performance of the resultant microcapsule.

<Second Coating Step>

[First-step Polycondensation]

The emulsion dispersion liquid containing the coacervate-coated particles prepared in the emulsifying dispersion apparatus (8) is then supplied together with a separately formed amino resin prepolymer dispersion liquid to a first-step polycondensation vessel (10), preferably after being subjected to preliminary mixing in a mixing vessel (9). In the first-step polycondensation vessel (10), the polycondensation of the amino resin prepolymer is caused, and simultaneously the coacervate-coated core material particles are coated with a second coating layer comprising the resultant polycondensate.

(Amino Resin Prepolymer)

The amino resin prepolymer used in the second coating step is an (unsubstituted or substituted) methylol derivative formed by an addition reaction between a polyamino compound, such as (thio)urea, melamine or benzoguanamine, and an aldehyde compound, such as formaldehyde, acetaldehyde or glutaraldehyde.

In the system example of FIG. 1, an embodiment of forming a second coating layer of a composite film from two species of a urea resin prepolymer and a melamine resin prepolymer. Referring to FIG. 1, urea (aqueous solution)

(11) and formalin (12) in a prescribed ratio are supplied via respective metering pumps (11p, 12p) to the bottom of a urea resin prepolymer reaction vessel (13) so that the resultant urea resin prepolymer liquid is withdrawn from an upper part of the vessel (13). Further, melamine (aqueous dispersion) (14) and formalin (12) in a prescribed ratio are supplied via respective metering pumps (14p, 12pp) to the bottom of a melamine resin prepolymer reaction vessel (15) so that the resultant melamine resin prepolymer liquid is withdrawn from an upper part of the vessel (15) and is supplied together with the urea resin prepolymer liquid from the vessel (13) to the mixing vessel (9) (or the first-step polycondensation vessel (10)).

In order to provide a microcapsule product with a stable quality, it is necessary to control the polycondensation velocity (methylene bridge formation velocity) at an optimal value, thereby controlling the tightness of the resultant coating film. It has been found that the methylene bridge formation velocity is largely affected by the degree of methylolation. Accordingly, in the embodiment of FIG. 1, the reaction vessels (13 and 15) are separately provided for independently controlling the resin prepolymer formation steps which are the methylolation steps with respect to the urea resin prepolymer and the melamine resin prepolymer. The reaction vessels (13 and 15) are respectively a vertical reaction vessel equipped with flat paddle-type stirring blades. In the reaction vessel (15), partitioning plates are provided only to an upper half of the vessel so as to prevent the precipitation of yet-unreacted melamine particles in a lower half of the vessel (15).

The resin prepolymer forming conditions may include a pH of 5–9, preferably 7–9, further preferably 7.5–8.5, in view of the stability of methylolation degree. Outside the above ranges, i.e., excessively acidic or alkaline, the resultant microcapsules are liable to be aggregated. The reaction temperature for the urea resin prepolymer formation may be 50–80° C., preferably 60–75° C., and the reaction temperature for the melamine resin prepolymer formation may be 40–70° C., preferably 50 –65° C., respectively in view of the stability of methylolation degree.

The microcapsule according to the present invention may have an average particle size (diameter) arbitrarily selected in a range of 1–100 μm, preferably 2–20 μm, and a coating film thickness arbitrarily changeable in a range of 0.05–3 μm. The microcapsule produced according to the present invention can exhibit a core material elusion rate (velocity) into water through the microcapsule film which can be controlled as desired. The control can be achieved by changing a proportion of formamide in the resin prepolymer, by changing an amount of the resin prepolymer relative to the core material, or by changing ratios among urea, melamine and/or benzoquinamine resin prepolymers. The ratio between formaldehyde and urea, melamine or benzoguanamine constituting the second coating resin may greatly affect the overall performances of the product microcapsule. The formaldehyde may be contained in 0.6–4.0 mol, preferably 0.8–3.0 mol, per 1 mol of urea; 1.0–9.0 mol, preferably 1.6–7.0 mol, per 1 mol of melamine; and 0.6–4.0 mol, preferably 0.8–4.0 mol per 1 mol of benzoguanamine. The ratio(s) among urea, melamine and benzoguanamine can be arbitrarily selected so as to provide the microcapsule coating film with a tightness and a thickness controlled for providing a film strength, a permeability and a core material elution rate into water suitable for intended usages. The resin prepolymer may preferably be used for film formation in a range of 0.02–1.0 g per 1 g of the core material.

(First-step Polycondensation)

The dispersion liquid containing the coacervate-coated core material particles and the amino resin prepolymer (methylol derivative) liquids from the reaction vessels (13 and 15), respectively introduced into the first-step polycondensation vessel (10), preferably via the mixing vessel (9), are first subjected to methylene bridge formation (methylation or polycondensation) due to conversion from the methylol derivative by adding a relatively low concentration of acid catalyst (16) (e.g., 10%-citric acid aqueous solution), whereby the methylation product is deposited onto the peripheral surfaces of the coacervate-coated core material particles to initiate the second coating film formation. During this period, a remarkable viscosity increase can possibly occur in the reaction vessel (10), so that dilution water is introduced thereinto via a metering pump (4pp) to suppress the viscosity increase of the system. During the first-step polycondensation, the pH may be controlled in a range of 2–7, preferably 2–5, and the reaction temperature may be controlled in a range of 15–80° C., preferably 30–70° C.

The first-step polycondensation vessel (10) may preferably be a vertical reaction vessel equipped with flat paddle-type stirring blades, and the stirring blade peripheral speed may preferably be in a range of 0.6–2.0 m/sec. Too low a peripheral speed is liable to cause aggregation of the microcapsules, and an excessively large peripheral speed can obstruct the effective film formation because the gathering of the resultant polycondensate of the amino resin prepolymer is liable to be obstructed thereby.

[Second-step Polycondensation]

Then, the dispersion liquid withdrawn from the first step polycondensation vessel (10) and containing microcapsules partially coated with the polycondensate (methylation product) of the amino resin prepolymer is further supplied to second-step polycondensation vessels (18a–18d) connected in series, where the coating by deposition of the methylation product is completed, and a dispersion liquid (19) containing the product microcapsule is recovered from a final reaction vessel (18d). The microcapsule-containing liquid can be used for various usages as it is. Alternatively, the dispersion can be further subjected to dehydration, drying and further classification, as desired, to obtain a powdery product microcapsule. The second-step polymerization is a process for providing a period of time required to complete the necessary polycondensation and complete the stable film formation. The period for residence within the second-step polycondensation vessels (18a–18d) may preferably be sufficient to provide 10–96 hours, more preferably ca. 15–48 hours, in total with the residential time in the first-step polycondensation vessel (10). The reaction temperature for the second-step polycondensation may be 15–80° C., preferably 30–70° C., and the pH may be 2–7, preferably 2–5. For this purpose, it is preferred that a relatively high concentration of acid catalyst (17) (e.g., 30%-citric acid aqueous solution) is added to any of the second-step polycondensation vessels (18a–18d). Incidentally, the second-step polycondensation is a long period of relatively mild reaction, so that it is possible to dispose a plurality of batch-wise reaction vessels each having a relatively large volume which is commensurate with the discharge capacity of the first-step polycondensation vessel (10) and proceeding with the second-step polymerization batch-wise by receiving the discharge liquid from the vessel (10) in one of the plurality of vessels to be alternately used by switching.

In the above, an embodiment of using a continuous production apparatus has been described as a preferred embodiment of the process for producing a microcapsule according to the present invention. This embodiment is preferred in order to provide microcapsules having a uniform coating film in a good particle size distribution. However, for the purpose of producing a microcapsule having a uniform coating film while suppressing the occurrence of aggregate of isolated film material and the presence of isolated core material, the use of a continuous production apparatus is not necessarily essential as far as it allows the practice of a process including a first coating step of coating the core material with a coacervate of the water-soluble cationic amino resin and the anionic surfactant, and a second coating step of adding an amino resin prepolymer to the resultant aqueous dispersion liquid containing the resultant coacervate-coated core material particles and forming a second coating film comprising the polycondensate thereof.

Particularly, the first-step polycondensation and the second-step polycondensation performed by receiving the dispersion liquids supplied from the emulsifying dispersion apparatus (8) and the prepolymer reaction vessels (13 and 15) can be performed in a batch-wise reaction vessel to effect good microencapsulation by controlling the temperature, pH and stirring speed, according to necessity, (as shown in Example 5 described hereinafter).

According to the microcapsule production process as described above of the present invention, it is possible to produce a microcapsule according to the present invention comprising core material particles successively coated with (i) a solidified layer of coacervate of a water-soluble cationic amino resin and an anionic surfactant, and (ii) a layer of polycondensate of amino resin prepolymer, in a (volume-average) particle size of 1–100 $\mu$m, preferably 2–20 $\mu$m, and a total coating layer thickness of 0.05–3 $\mu$m, with a small fluctuation in particle size, a narrow particle size distribution, suppressed formation of isolated core material and a high yield.

Figure 3:
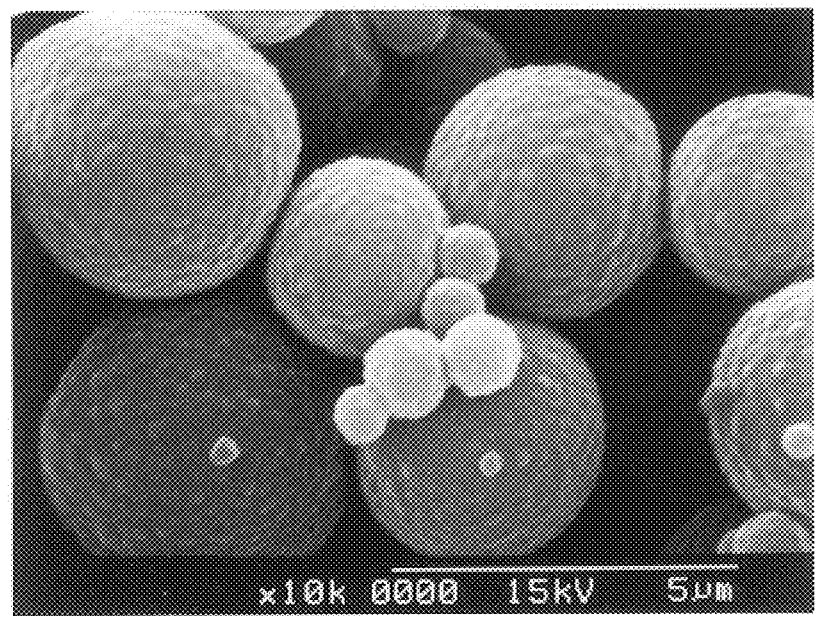
Figure 4:
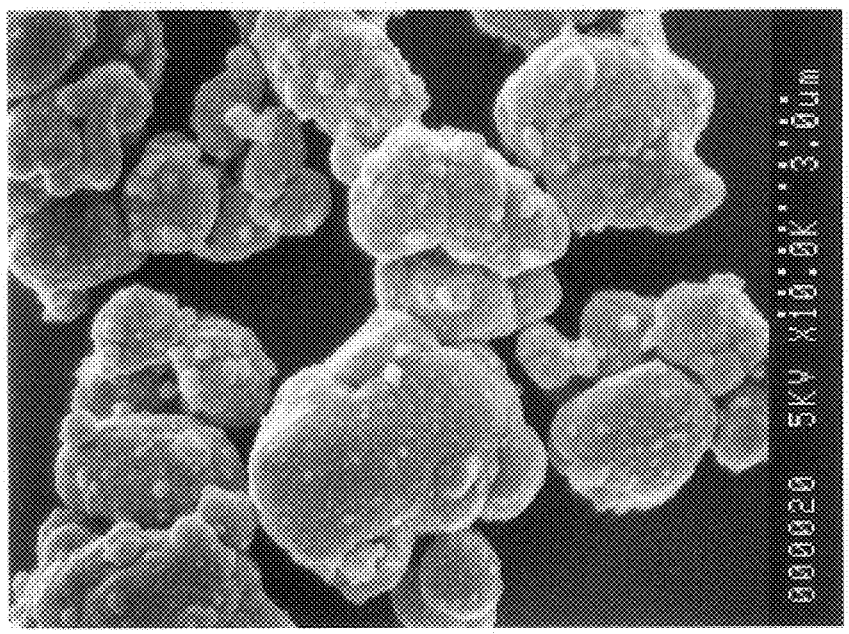
Figure 5:
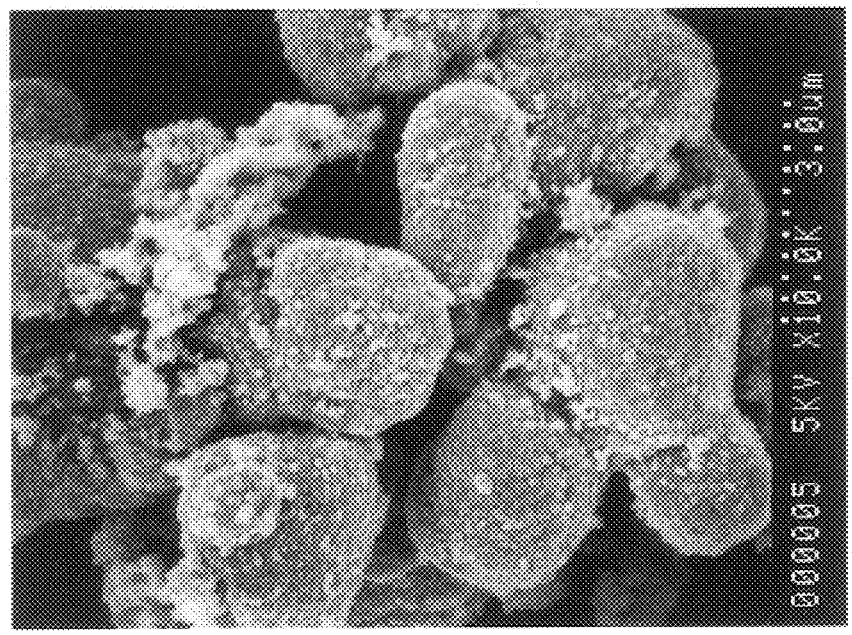
Figure 6:
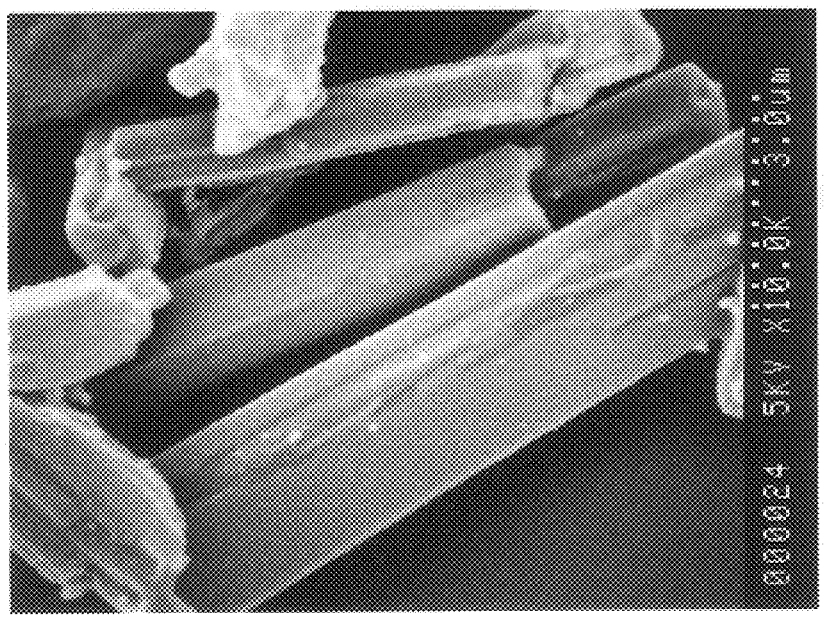
Figure 7:
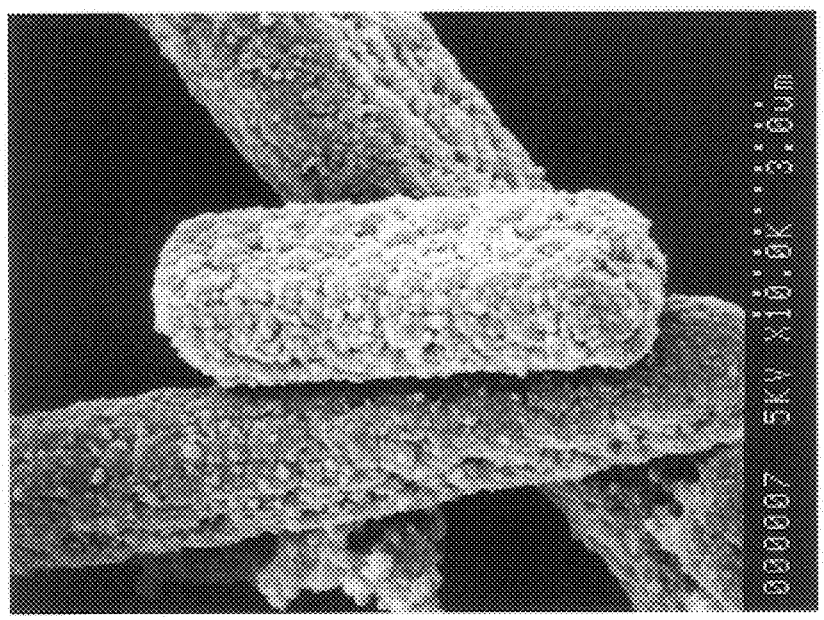

As mentioned above, a characteristic of the microcapsule according to the present invention is that the coating layer includes (i) a solidified coacervate layer and (ii) an amino resin prepolymer polycondensate layer forming orderly laminar layers (i.e., layers which are substantially parallel to the outer shape of an individual particle of core material). Such an orderly laminar layer structure has been confirmed by a microcapsule outer shape which is substantially similar to an outer shape of the core material, and further a similarity in shape of the boundary between the layers (i) and (ii) to the outer shape of the core material by microscopic observation. In other words, a microcapsule of the present invention is characterized in that the outer circumference thereof is substantially free from a surface projection or attachment comparable to the coating layer thickness (of 0.05–3 $\mu$m, preferably 0.05–1.5 $\mu$m). A part of such a morphological characteristic of the microcapsule according to the present invention may be observed in FIGS. 2, 4 and 6 which are scanning electron microscope (SEM) photographs (×10,000) of microcapsules prepared in Examples according to the present invention in comparison with FIGS. 3, 5 and 7 which are SEM photographs (×10,000) of microcapsules prepared in Comparative Examples according to the process of the above-mentioned GB-A 2113170. Such an orderly laminar coating layer structure of the microcapsule according to the present invention has been obtained through the process of the present invention wherein a solidified layer (i) of coacervate of a water-soluble cationic amino resin and an anionic surfactant is first formed as a primer coating layer on the particulate core material and then further coated with a layer (ii) of amino resin prepolymer polycondensate in contrast with the process of GB-A 2113170 wherein such a water-soluble cationic amino resin and an anionic surfactant are used as agents for improving the affinity between a particulate core material and a coating amino resin prepolymer to form a single coating layer of the amino resin prepolymer polycondensate also containing the affinity-improving agents. Further, from a viewpoint of process, in the process of GB-A 2113170, the water-soluble cationic amino resin is mixed with the anionic surfactant (and further with the amino resin prepolymer) in an aqueous medium, and thereafter the particulate core material is added to the aqueous medium containing the mixture, whereas the process of the present invention includes a characteristic two-step coating process including a first coating step wherein a water-soluble cationic amino resin and an anionic surfactant are mixed with each other in the presence of a particulate core material so as to immediately coat the particulate core material with the as-produced coacervate formed by the mixing, preferably by accomplishing the dispersion of the coacervate-forming agents and the core material within a very short period (preferably within 3 seconds, more preferably within 1 second) from the start of the mixing of the coacervate-forming agents, thereby forming a uniform coating layer of the coacervate on the particulate core material and solidifying the coacervate by the presence of an acid catalyst, and thereafter effecting a second coating step of adding and mixing an amino resin prepolymer.

Figure 2:
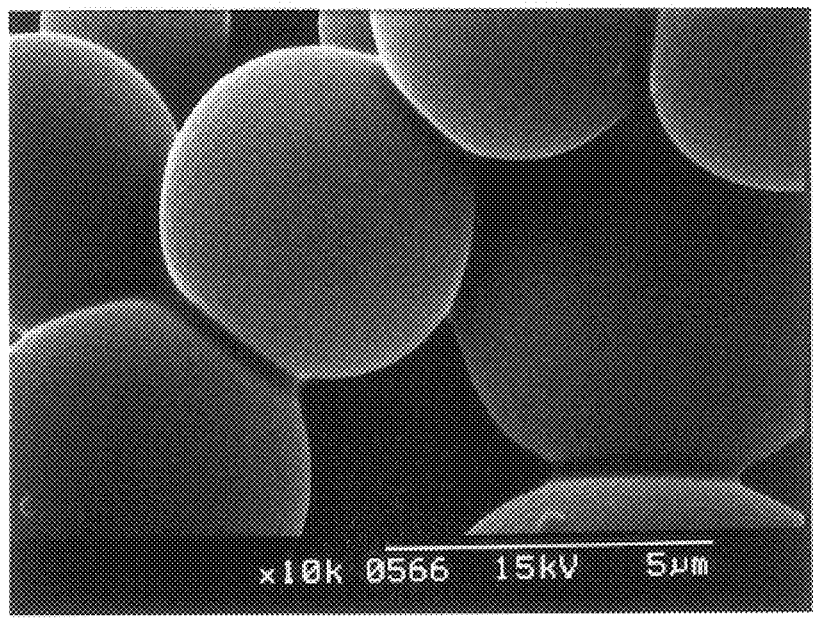
FIGS. 2 to 7 are microscopic photographs (each in a magnification of $1 \times 10^4$) of microcapsules prepared in Example 1, Comparative Example 1, Example 3, Comparative Example 3, Example 4 and Comparative Example 4, respectively.

Further, in the case of using a liquid core material in the present invention, it is possible to produce microcapsules having a shape close to a true sphere and a very smooth surface (as shown in FIG. 2 for a microcapsule obtained by Example 1 described hereinafter).

The thus-produced microcapsule in the form of a slurry can be used as it is. However, in order to provide a microcapsule with a good state of coating film, it is necessary to add an excessive amount of formaldehyde in the above-mentioned process, so that the product microcapsule (slurry) still contains a substantial amount of residual formaldehyde.

As such a formaldehyde-containing slurry generates a gaseous substance (mainly, formaldehyde) having a peculiar pungent odor which can give an unpleasant feeling to human body and adversely affect the operation environment, it is sometimes desirable to remove the residual formaldehyde through various chemical processes inclusive of the formose process wherein the residual aldehyde is self-condensed or saccharified into formose at an elevated temperature and an alkaline pH of e.g., 10–12.5 by addition of an alkaline substance, such as caustic soda or slaked lime, optionally in the presence of one or more other saccharides, such as glucose, fructose, lactose and glycerin aldehyde; a process wherein the residual aldehyde is converted into hexamethylenetetramine by addition of ammonia or salts thereof; a process wherein the residual formaldehyde is reacted with sodium sulfite; and a process wherein the residual aldehyde is reacted with hydroxylamine hydrochloride and a strong base at a pH of 7 or higher.

The thus-produced microcapsule (slurry) can be used as it is but may ordinarily be stabilized for subsequent use as an aqueous suspension by addition of a thickening agent, an anti-freezing agent, a dispersing agent, a specific gravity-adjusting agent, etc. Further, it is also possible to convert the slurry into a fine powder form of microcapsule, e.g., by spray-drying. Further, it is also possible to obtain a granular or agglomerated form of microcapsules by blending the powdery or slurry microcapsules with a solid diluent or carrier and optionally with a surfactant in a known manner.

Hereinbelow, the present invention will be described more specifically based on Examples and Comparative Examples.

EXAMPLE 1

A microcapsule according to the present invention was prepared by using an apparatus system as substantially shown in FIG. 1.

(First Coating Step)

A core material (1) of chlorpyrifos (an insecticide, liquid at 45° C., available under a trade name of "LENTREK" from Dow Chemical Co.) and an anionic surfactant (2) of 1% aqueous solution of sodium dodecylbenzenesulfonate ("NEOPELEX available from Kao K.K.) were provided so as to be supplied at rates of 78 kg/h and 9.0 kg/h, respectively.

Separately, warm water (at 50° C.) (4) at 110 kg/h, cationic urea resin (3) ("U-RAMIN P-1500", in the form of an aqueous solution (solid content=ca. 40 wt. %), available from Mitsui Kagaku K.K.) at 7.9 kg/h and a 5%-aqueous solution of triethanolamine $(N(EtOH)_3)$ (5) at 6.5 kg/h were supplied to an emulsion mother liquid mixing vessel (7) and mixed with each other therein, and then the pH of the mixture was adjusted to 4.75 by adding a 5%-citric acid (CA) aqueous solution (6) as an acid catalyst. The thus pH-adjusted mixture liquid at 50° C. was continuously supplied together with the above-mentioned core material (1) and anionic surfactant aqueous solution (2) to an emulsifying dispersion apparatus (8) (having an inner volume of ca. 0.5 liter and providing a residence time of 7–10 sec., "TK-HI-Line Mill HL-50 type", available from Tokushu Kika Kogyo K.K.) wherein the dispersion conditions were set to provide a liquid droplet average-particle size of 3 –5 µm at 45° C., thereby obtaining a dispersion liquid containing coacervate-coated core material particles.

(2) Preparation of Amino Resin Prepolymer

A 30%-urea aqueous solution (11) at 15.2 kg/h and formalin (37%-formaldehyde aqueous solution adjusted to pH 8.0 by addition of 20%-triethanolamine aqueous solution) (12) at 11.1 kg/h were supplied to a resin prepolymer reaction vessel (13), and were caused to reside therein for 70 min. at 70° C. under stirring to continuously produce a urea resin prepolymer (formaldehyde/urea=1.8 (by mol)) liquid.

Separately, a 18%-melamine aqueous dilution liquid at 32.9 kg/h and formaline (adjusted to ph 8.0 by addition of 20%-triethanolamine aqueous solution) (12) at 19.1 kg/h were supplied to a resin prepolymer reaction vessel (15) and were caused to reside therein for 35 min. at 50° C. under stirring to continuously produce a melamine resin prepolymer (formaldehyde/melamine=4 (by mol)) liquid.

(3) Second Coating Step (Microencapsulation)

The dispersion liquid prepared in the step (1) mentioned above and the resin prepolymer liquids (13 and 15) prepared in the step (2) above were continuously and uniformly mixed each other in a mixing vessel (9), and the resultant mixture liquid was introduced into a first-step polycondensation vessel (10), to which an acid catalyst of 10%-citric acid aqueous solution was added so as to continuously adjust the pH at 4.75. After residence for ca. 10 min. therein, warm water (4) was continuously added thereto at a rate of 50 kg/h, and the system was held at 50° C. under stirring for a residence time of 30 min. Then, the effluent liquid from the vessel (10) was then supplied to a first second-step polycondensation vessel (18a) for 5 hours of stirring at 50° C. therein, followed by 5 hours of stirring at 50° C. in a second vessel (18b) while adding an acid catalyst of 30%-citric acid aqueous solution (17) at a rate of 3 kg/h so as to continuously adjust the pH to 2.8, and further 5 hours each of stirring at 50° C. in third and fourth vessels (18c and 18d) to complete the microencapsulation.

EXAMPLE 2

Microencapsulation was performed substantially in a similar manner as in Example 1 except for the following modifications.

The first coating step was repeated except for changing the core material (1) to 60 kg/h of ethoprophos in an undiluted form ("MOCAP", an insecticide available from Rhone-Poulenc Agrochimie), and supplying 118.0 kg/h of the warm water (4), 8.3 kg/h of the water-soluble cationic urea resin (3) ("U-RAMIN P-1500") and 8.0 kg/h of the anionic surfactant (1% "NEOPELEX" aqueous solution). The preparation of the amino resin prepolymers was repeated except for supplying 19.0 kg/h of the 30%-urea aqueous solution (11) and 13.86 kg/h of the formalin (12) for preparation of urea resin prepolymer, and 30.8 kg/h of the 18%-melamine aqueous dilution (14) and 14.28 kg/h of the formalin (12) for preparation of melamine resin prepolymer. Thereafter, the first and second polycondensation reactions were repeated in the same manner as in Example 1 to complete the microencapsulation.

EXAMPLE 3

Microencapsulation was performed substantially in a similar manner as in Example 1 except for the following modifications.

The first coating step was repeated except for changing the core material (1) to 70.0 kg/h of carbaryl ("NAC", an insecticide available from Rhone-Poulenc Agrochimie), and supplying 118.0 kg/h of the warm water (4), 8.7 kg/h of the water-soluble cationic urea resin (3) ("U-RAMIN P-1500") and 10.0 kg/h of the anionic surfactant (1% "NEOPELEX" aqueous solution). The preparation of the amino resin prepolymers was repeated except for supplying 22.8 kg/h of the 30%-urea aqueous solution (11) and 16.6 kg/h of the formaline (12) for preparation of urea resin prepolymer, and 37.0 kg/h of the 18%-melamine aqueous dilution (14) and 17.1 kg/h of the formalin (12) for preparation of melamine resin prepolymer. Thereafter, the first and second polycondensation reactions were repeated in the same manner as in Example 1 to complete the microencapsulation.

EXAMPLE 4

Microencapsulation was performed substantially in a similar manner as in Example 1 except for the following modifications.

The first coating step was repeated except for changing the core material (1) to 84.0 kg/h of dichlobenil ("DBN", a herbicide available from Uniroyal, Inc.) and supplying 208.8 kg/h of the warm water (4), 8.6 kg/h of the water-soluble cationically modified urea resin (3) ("U-RAMIN P-1500") and 10.0 kg/h of the anionic surfactant (1% "NEOPELEX" aqueous solution). The preparation of the amino resin prepolymers was repeated except for supplying 9.5 kg/h of the 30%-urea aqueous solution (11) and 7.0 kg/h of the formaline (12) for preparation of urea resin prepolymer, and 15.4 kg/h of the 18%-melamine aqueous dilution (14) and 7.1 kg/h of the formalin (12) for preparation of melamine resin prepolymer. Thereafter, the first and second polycondensation reactions were repeated in the same manner as in Example 1 to complete the microencapsulation.

COMPARATIVE EXAMPLE 1

Microencapsulation of chlorpyrifos (as an insecticide) was performed as follows, i.e., substantially in the same manner as the process disclosed in GB-A 2113170.

(1) Preparation of Amino Resin Prepolymer 8.9 kg of urea and 20.5 kg of formalin (37%-formaldehyde aqueous solution adjusted to pH 8.5 with triethanolamine) were mixed under stirring and allowed to react with each other for 60 min. at 70° C. to form a urea resin prepolymer (formaldehyde/urea=1.8 (by mol)) liquid.

Separately, 4.3 kg of melamine and 10.4 kg of formalin (adjusted to pH 8.5 by addition of 2%-NaOH aqueous solution) were mixed together with 15.3 kg of warm water under stirring and allowed to react with each other for 30 min. at 50° C. to form a melamine resin prepolymer (formaldehyde/melamine=4 (by mol)) liquid.

(2) Formation of Liquid Droplets (Emulsion Dispersion)

29.4 kg of the urea resin prepolymer liquid and 30 kg of the melamine resin prepolymer liquid prepared in the step (1) above, 6.1 kg of water-soluble cationic urea resin ("U-RAMIN P-1500"), 6.1 kg of 5%-triethanolamine aqueous solution and 56.0 kg of 0.25%-aqueous solution of polyethylene oxide (as a thickener) ("ALCOX", available from Meisei Kagaku Kogyo K.K.) were mixed under stirring in a vessel, followed by addition of 25%-citric acid aqueous solution to adjust the system pH to 4.75 and addition of 0.69 kg of 10%-aqueous solution of sodium dodecylbenzene-sulfonate ("NEOPELEX", available from Kao K.K.).

To the liquid system, 77.3 kg of chlorpyrifos (as a core material) was added, and the system was stirred batchwise by means of a high-speed emulsion dispersion stirrer ("TK-HOMOMIXER", available from Tokushu Kika Kogyo K.K.) so as to form an emulsion dispersion liquid containing dispersed liquid droplets in an average particle size of 3–6 μm.

(3) Film Formation (Microencapsulation)

The emulsion dispersion liquid containing the liquid droplets formed in the step (2) above was transferred into a polycondensation vessel and held therein under stirring at 50° C. After lapse of 20 min., 70 kg of warm water was added thereto, and the system was further held at 50° C under stirring for 24 hours, followed by addition of 10%-citric acid aqueous solution to adjust the system pH to 2.8 and further 48 hours of stirring at 50° C. to complete the microencapsulation.

COMPARATIVE EXAMPLE 2

The process of Comparative Example 1 was repeated except for using 51.3 kg of the 0.25%-aqueous solution of polyethylene oxide ("ALCOX"), 0.9 kg of the 10%-aqueous solution of sodium dodecylbenzene sulfonate ("NEOPELEX") and 8.0 kg of the water-soluble cationic urea resin ("U-RAMIN P-1500") for liquid droplet formation; and changing the core material to 60 kg of ethoprophos, to effect the microencapsulation.

COMPARATIVE EXAMPLE 3

The process of Comparative Example 1 was repeated except for using 6.8 kg of urea and 16.5 kg of the formalin for preparation of urea resin prepolymer; using 6.6 kg of melamine, 17.0 kg of the formalin and 30.2 kg of warm water for preparation of melamine resin prepolymer; using 64.0 kg of the 0.25%-aqueous solution of polyethylene oxide ("ALCOX"), 0.98 kg of the 10%-aqueous solution of sodium dodecylbenzenesulfonate ("NEOPELEX") and 6.6 kg of the water-soluble cationic urea resin ("U-RAMIN P-1500") for liquid droplet formation; and changing the core material to 70 kg of carbaryl, to effect the microencapsulation.

COMPARATIVE EXAMPLE 4

The process of Comparative Example 1 was repeated except for using 2.8 kg of urea and 7.0 kg of the formalin for preparation of urea resin prepolymer; using 2.8 kg of melamine, 7.1 kg of the formalin and 12.6 kg of warm water for preparation of melamine resin prepolymer; using 66.0 kg of the 0.25%-aqueous solution of polyethylene oxide ("ALCOX"), 10.0 kg of the 10%-aqueous solution of sodium dodecylbenzene sulfonate ("NEOPELEX") and 8.6 kg of the water-soluble cationic urea resin ("U-RAMIN P-1500") for liquid droplet formation; and changing the core material to 84 kg of dichlobenil, to effect the microencapsulation.

COMPARATIVE EXAMPLE 5

For the formation of liquid droplets, 12.9 kg of water-soluble cationic urea resin ("U-RAMIN P-1500") and 123.1 kg of warm water were mixed in a vessel, and after adding a 10%-citric acid aqueous solution to pH 5.0, 1.3 kg of sodium dodecylbenzenesulfonate ("NEOPELEX") was added thereto.

Into the liquid prepared above, 77.3 kg of chlorpyrifos (as a core material) was added, and the system was stirred batchwise by means of a high-speed stirrer ("TK-HOMOMIXER") so as to form an emulsion dispersion liquid containing dispersed liquid droplets in an average particle size of 3–6 μm similarly as in Comparative Example 1.

The emulsion dispersion liquid containing the liquid droplets formed in the above step was transferred into a polycondensation vessel and held therein under stirring at 50° C. Into the system, 29.4 kg of a urea resin prepolymer liquid and 30.0 kg of a melamine resin prepolymer liquid, respectively prepared in the same manner as in Comparative Example 1, were added, and a 10%-citric acid aqueous solution was added thereto to adjust the pH to 4.75. Thereafter, the microencapsulation (film formation) step was caused to proceed and completed similarly as in Comparative Example 1.

[Comparative Performance Evaluation Tests]

The microcapsules prepared in the above Examples 1–4 and Comparative Examples 1–5 were subjected to measurement of the following properties for the purpose of comparison.

(1) Average Particle Size (Of Microcapsules)

Into a 30 ml-Erlenmeyer flask equipped with a plug, 20 ml of pure water is placed, and a microcapsule sample (e.g., in the form of a dispersion liquid thereof) is added thereto so as to provide a microcapsule content of ca. 2 wt. %. The flask is subjected to 1 min. of vibration at a rate of 120 reciprocations/min. at room temperature. Thereafter, ca. 10 ml of the dispersion liquid sample is injected into a sample pass of a laser diffraction-type particle size distribution meter ("Model LA-500", available from Horiba Seisakusho K.K.) to obtain a particle size distribution, from which a volume-average particle size (diameter) is calculated. The results are shown in Table 1.

(2) Amount of Eluted Core Material in Water

For evaluating the gradual liberation characteristic of a sample microcapsule (rate of liberation of a content material through a microcapsule film), the sample microcapsule is dispersed in water, and the amount of the core material eluted into the water after standing for 24 hours is measured in the following manner.

An amount of sample microcapsule (dispersion liquid) containing 50 mg of an effective component (core material) is sampled into a 200 ml-Erlenmeyer flask equipped with a plug, and 100 ml of pure water is added thereto. After tight plugging, the flask is set in an incubator vibrator and and subjected to 2 min. of vibration at a rate of 120 reciprocations/min. on a water bath of 30° C., and then left standing for 24 hours in a thermostat bath of 30° C. A portion of the aqueous phase alone is taken out and sufficiently mixed with acetonitril added thereto. The mixture liquid is injected into a high-performance liquid chromatograph (HPLC) to measure the content of the core material eluted into water. The results are shown in Table 2.

(3) Amount of Isolated Core Material Present in a Microcapsule Aqueous Dispersion Liquid An amount of microcapsule dispersion liquid sample containing ca. 0.2 g of effective component (core material) is taken into a 50 ml-Erlenmeter flask and 20 ml of water is added thereto. After 2 min. of shaking the flask at a rate of 120 reciprocations/min. by means of a universal shaker ("Vibrator SA 300", available from Yamato Kagaku K.K.), the content of the flask is filtrated through filter paper ("No. 5c", available from Toyo Roshi K.K.). Then, 0.5 ml of the filtrate liquid is taken into a 5 ml-glass vessel equipped with a plug by using a hole pipet and then 1 ml of acetonitril is added thereto for sufficient mixing. The mixture is injected into a high-performance liquid chromatograph to measure the content of the isolated core material in the microcapsule dispersion liquid. The results are shown in Table 3.

(4) Amount of Core Material in Microcapsule 0.2 g of a microcapsule sample is weighed in a 100 ml-Erlenmeyer flask, and 0.1 ml of hydrochloric acid and 20 ml of acetone are added thereto. After attaching a cooling tube thereto, the content of the flask is subjected to 60 min. of refluxing on a water bath of 50° C. The reflux liquid is then cooled, and an internal standard solution (di-n-propyl phthalate solution in acetone) is added and sufficiently mixed therewith. The mixture is injected into a gas chromatograph to measure the amount of core material in 0.2 g of microcapsule from which the amount of core material in the total product microcapsule is calculated. A percentage microencapsulation is calculated from the following equation:

Percentage microencapsulation (%)=(Amount of core material in the total product microcapsule/Amount of charged core material)×100.

The results are shown in Table 4.

Each of the above Examples and Comparative Examples was repeated 5 times generally on different days, and Tables 1–4 shown below list the results of the above measurements with respect to the product microcapsule obtained in the 5 times of the tests and average values thereof.

(5) Surface States of Microcapsules

Some product microcapsules were photographed through a scanning electron microscope (SEM), and photographs (each in a magnification of $10^4$) of microcapsule products obtained in Example 1, Comparative Example 1, Example 3, Comparative Example 3, Example 4 and Comparative Example 4 are attached hereto as FIGS. 2–7, respectively.

TABLE 1

Average particle size ($\mu$m) of microcapsules

| | Core material | | | | | | | |
|---|---|---|---|---|---|---|---|---|
| | Chlorpyrifos | | | Ethoprophos | | | NAC (carbaryl) | | DBN (dichlobenyl) |
| | | | | Example | | | | |
| Test No. | 1 | Comp. 1 | Comp. 5 | 2 | Comp. 2 | 3 | Comp. 3 | 4 | Comp. 4 |
| 1 | 4.4 | 5.9 | 7.2 | 3.9 | 4.1 | 5.4 | 6.3 | 4.6 | 6.4 |
| 2 | 4.4 | 6.5 | 6.8 | 4.0 | 5.9 | 5.6 | 6.7 | 4.4 | 7.5 |
| 3 | 4.5 | 5.0 | 5.4 | 4.0 | 7.1 | 5.8 | 7.1 | 4.4 | 19.0 |
| 4 | 4.4 | 8.2 | 9.3 | 3.7 | 7.7 | 5.5 | 6.6 | 4.9 | 8.8 |
| 5 | 4.9 | 10.7 | 8.2 | 3.9 | 4.0 | 5.6 | 7.9 | 4.2 | 21.3 |
| Ave. | 4.5 | 7.3 | 7.4 | 3.9 | 5.8 | 5.6 | 6.9 | 4.5 | 12.6 |

TABLE 2

Eluted core material in water (ppm) after 24 hours

| | Core material | | | | | | | | |
|---|---|---|---|---|---|---|---|---|---|
| | Chlorpyrifos | | | Ethoprophos | | | NAC (carbaryl) | | DBN (dichlobenyl) |
| | | | | Example | | | | | |
| Test No. | 1 | Comp. 1 | Comp. 5 | 2 | Comp. 2 | 3 | Comp. 3 | 4 | Comp. 4 |
| 1 | 0.3 | 1.1 | 1.5 | 13.1 | 70.7 | 5.3 | 9.3 | 4.1 | 16.2 |
| 2 | 0.4 | 1.1 | 1.3 | 12.8 | 86.3 | 6.0 | 7.7 | 5.7 | 7.9 |
| 3 | 0.3 | 1.0 | 2.1 | 12.1 | 142.7 | 5.4 | 12.4 | 4.5 | 11.3 |
| 4 | 0.3 | 2.6 | 1.8 | 12.9 | 79.1 | 5.4 | 20.9 | 5.2 | 12.1 |
| 5 | 0.3 | 1.3 | 1.8 | 11.0 | 81.7 | 5.0 | 7.6 | 4.9 | 10.7 |
| Ave. | 0.3 | 1.4 | 1.7 | 12.4 | 90.1 | 5.4 | 11.6 | 4.9 | 11.6 |

TABLE 3

Amount of isolated core materials in water (ppm)

| | Core material | | | | | | | | |
|---|---|---|---|---|---|---|---|---|---|
| | Chlorpyrifos | | | Ethoprophos | | NAC (carbaryl) | | DBN (dichlobenyl) | |
| | | | | Example | | | | | |
| Test No. | 1 | Comp. 1 | Comp. 5 | 2 | Comp. 2 | 3 | Comp. 3 | 4 | Comp. 4 |
| 1 | 0.3 | 1.6 | 1.4 | 739 | 2060 | 39.8 | 129.6 | 27.8 | 61.9 |
| 2 | 0.3 | 0.7 | 1.7 | 740 | 2500 | 45.6 | 103.4 | 29.3 | 40.5 |
| 3 | 0.3 | 1.2 | 0.9 | 660 | 2460 | 55.8 | 75.8 | 27.1 | 46.4 |
| 4 | 0.4 | 0.7 | 1.2 | 667 | 2350 | 53.8 | 95.0 | 30.2 | 58.4 |
| 5 | 0.4 | 0.6 | 1.4 | 660 | 2320 | 45.4 | 88.4 | 28.9 | 46.4 |
| Ave. | 0.3 | 1.0 | 1.3 | 695 | 2340 | 48.4 | 98.4 | 28.7 | 50.7 |

TABLE 4

Percentage microencapsulation (of core material) (%)

| | Core material | | | | | | | | |
|---|---|---|---|---|---|---|---|---|---|
| | Chlorpyrifos | | | Ethoprophos | | NAC (carbaryl) | | DBN (dichlobenyl) | |
| | | | | Example | | | | | |
| Test No. | 1 | Comp. 1 | Comp. 5 | 2 | Comp. 2 | 3 | Comp. 3 | 4 | Comp. 4 |
| 1 | 96.8 | 89.0 | 88.7 | 97.8 | 89.5 | 96.9 | 87.7 | 95.7 | 85.4 |
| 2 | 97.3 | 88.7 | 88.8 | 97.7 | 89.1 | 97.2 | 88.0 | 95.4 | 85.3 |
| 3 | 98.1 | 88.9 | 88.7 | 98.1 | 89.9 | 97.1 | 87.6 | 95.1 | 86.0 |
| 4 | 97.2 | 89.1 | 89.1 | 97.6 | 89.7 | 96.9 | 87.9 | 95.8 | 85.7 |
| 5 | 98.1 | 89.3 | 89.1 | 97.8 | 89.3 | 97.4 | 87.3 | 95.5 | 85.1 |
| Ave. | 97.5 | 89.0 | 88.9 | 97.8 | 89.5 | 97.1 | 87.7 | 95.5 | 85.5 |

COMPARATIVE EXAMPLES 6–10, EXAMPLES 5–6

The microencapsulation process of Example 2 above was repeated while effecting the following modifications in respective Examples and Comparative Examples.

COMPARATIVE EXAMPLE 6

The operation corresponding to the first-coating step of Example 2 was repeated except for omitting the supply of the water-soluble cationic urea resin (3) ("U-RAMIN P-1500") and the anionic surfactant (2) (1%-aqueous solution of "NEOPELEX"), and the resultant dispersion liquid from the emulsifying dispersion apparatus (8) was supplied to the first-step polycondensation vessel (10) together with the urea resin prepolymer dispersion liquid (13) and the melamine resin prepolymer dispersion liquid (15), followed thereafter by the same microencapsulation as in Example 2, whereas the microcapsule film formation was failed.

COMPARATIVE EXAMPLE 7

The process of Comparative Example 6 was repeated except for supplying 8.3 kg/h of the water-soluble cationic urea resin (3) ("U-RAMIN P-1500") in the same manner as in Example 2 (but omitting the supply of the anionic surfactant (2) (1%-aqueous solution of "NEOPELEX") similarly as in Comparative Example 6), whereas the microcapsule film formation was failed similarly as in Comparative Example 6.

COMPARATIVE EXAMPLE 8

Microencapsulation was performed in a similar manner as in Example 2 except for omitting the supply of the water-soluble cationic urea resin (3) ("U-RAMIN P-1500"), and introducing the urea resin prepolymer dispersion liquid (13) and the melamine resin prepolymer dispersion liquid (15) prepared in the same manner as in Example 2 into the emulsifying dispersion apparatus (8) together with the core material 1 and the anionic surfactant (2) (1%-aqueous solution of "NEOPELEX") instead of the mixing vessel (9).

COMPARATIVE EXAMPLE 9

Microencapsulation was performed in the same manner as in Example 2 except for omitting the supply of the water-soluble cationic urea resin (3) ("U-RAMIN P-1500").

COMPARATIVE EXAMPLE 10

The microencapsulation process of Comparative Example 2 was substantially repeated.

EXAMPLE 5

The first coating step of Example 2 was repeated except for supplying the water-soluble cationic urea resin (3) ("U-RAMIN P-1500") at a rate of 0.83 kg/h, and in the second coating step of Example 2, introducing the effluent from the mixing vessel into a single batchwise polycondensation vessel to complete the microencapsulation in the polycondensation vessel while performing the addition of the 10%-citric acid aqueous solution (15) and the 30%-citric acid aqueous solution (17) and the control of temperatures for polycondensation thereafter in similar manners as in Example 2.

EXAMPLE 6

The microencapsulation process of Example 2 was substantially repeated.

[Measurement of Percentage Elution with Time]

Figure 8:
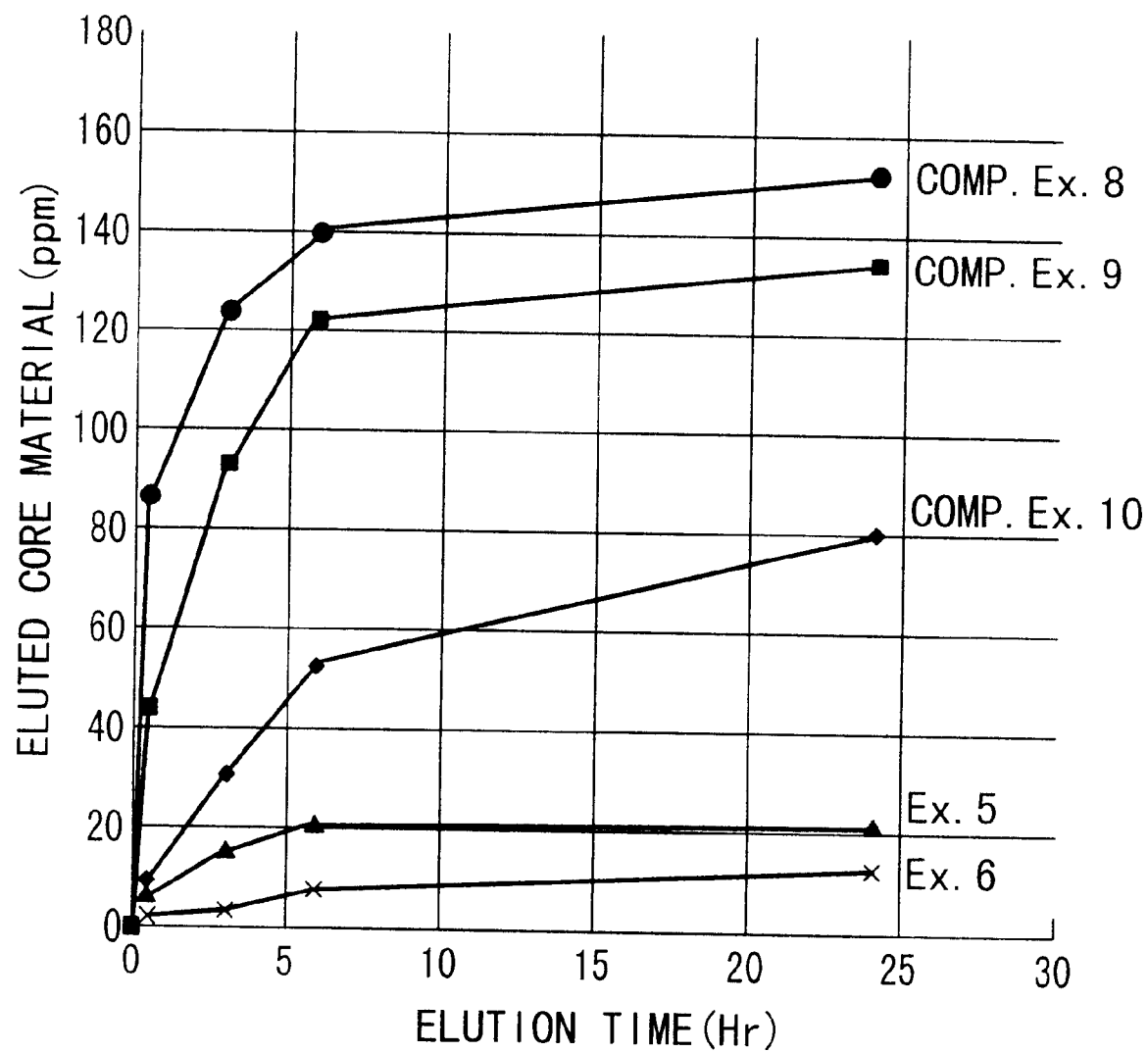
FIG. 8 is a graph showing measured rates of elution into water for microcapsules prepared in Comparative Examples 8, 9 and 10, and Examples 5 and 6.

The microcapsules prepared in the above-described Comparative Examples 8–10 and Examples 5–6 were subjected to the measurement of eluted core materials in the same manner as in (2) Amount of eluted core material in water described above but at time of 3 hours, 6 hours and 24 hours, respectively, from the start of the elution. The results of the measurements are plotted in FIG. 8 in terms of Eluted core material (ppm) in water versus the elution time.

As is apparent from the above-mentioned results of Examples and Comparative Examples, according to the present invention, a microcapsule having a uniform and smooth coating film and an excellent performance of gradually liberating the content material can be produced at a good particle size distribution and while suppressing the occurrence of isolated and aggregated film material, aggregated microcapsules and isolated core material, by coating the periphery of core material particles successively with (i) a solidified layer of coacervate of a water-soluble cationic amino resin and an anionic surfactant, and (ii) a layer of polycondensate of amino resin prepolymer.

What is claimed is:

1. A microcapsule, comprising a particulate core material, and a laminar coating layer including (i) a solidified layer of coacervate of a water-soluble cationic amino resin and an anionic surfactant, and (ii) a layer of polycondensate of amino resin prepolymer, successively coating the particulate core material, wherein the water-soluble cationic amino resin is a water-soluble cationic product of at least one amino resin selected from the group consisting of urea-aldehyde resin, melamine-aldehyde resin and guanamine-aldehyde resin.

2. A microcapsule according to claim 1, wherein the polycondensate of amino resin prepolymer comprises a polycondensate of prepolymer of at least one species of resin selected from the group consisting of urea resin, melamine resin and guanamine resin.

3. A microcapsule according to claim 2, wherein the amino resin prepolymer is a mixture of urea resin prepolymer and melamine resin prepolymer.

4. A microcapsule according to claim 1, wherein the water-soluble cationic amino resin is a water-soluble cationic urea-aldehyde resin.

5. A microcapsule according to claim 1, wherein the microcapsule has an average particle size of at most 100 $\mu$m.

6. A microcapsule according to claim 1, wherein the core material comprises an agricultural chemical.

7. A microcapsule according to claim 1, wherein the core material is a lubricant.

8. A microcapsule according to claim 1, wherein the core material is an inorganic material.

9. A microcapsule according to claim 1, wherein the core material is a color former.

10. A microcapsule according to claim 1, wherein the core material is a catalyst.

11. A process for producing a microcapsule, comprising:

a first coating step of mixing a water-soluble cationic amino resin and an anionic surfactant in the presence of a hydrophobic core material dispersed in an aqueous medium to coat the dispersed core material with a coacervate of the cationic amino resin and the anionic surfactant, wherein in the first coating step, an acid catalyst for promoting the coacervate to be formed and solidified is caused to be co-present in the aqueous medium to adjust a pH of 3–9, and a second coating step of adding an amino resin prepolymer into an aqueous dispersion liquid containing the coated dispersed core material and polycondensing the amino resin prepolymer to further coat the coated dispersed core material with a polycondensate of the amino resin prepolymer, wherein in the second coating step, the amino resin prepolymer is polycondensed at a pH 2–7 by addition of an acid catalyst, wherein the water-soluble cationic amino resin is a water-soluble cationic product of at least one amino resin selected from the group consisting of urea-aldehyde resin, melamine-aldehyde resin and guanamine-aldehyde resin.

12. A process according to claim 11, wherein the water-soluble cationic amino resin is a water-soluble cationic urea resin.

13. A process according to claim 11, wherein the acid catalyst is caused to be co-present in the aqueous medium to adjust a pH of 4–6.

14. A process according to claim 11, wherein the first coating step includes a step of continuously mixing an aqueous solution of the water-soluble cationic amino resin and an aqueous solution of the anionic surfactant, at least one of which contains the hydrophobic core material dispersed therein.

15. A process according to claim 14, wherein the hydrophobic core material is first dispersed in the aqueous solution of the anionic surfactant.

16. A process according to claim 11, wherein the amino resin prepolymer is a methylolation product of at least one amino resin selected from the group consisting of urea resin, melamine resin and guanamine resin.

17. A process according to claim 16, wherein the amino resin prepolymer comprises a mixture of methylolated urea resin and methylolated melamine resin.

18. A process according to claim 16, wherein the methylolation of the amino resin is performed at a pH 7–9.

* * * * *